US011544350B2

(12) United States Patent
Chida et al.

(10) Patent No.: US 11,544,350 B2
(45) Date of Patent: Jan. 3, 2023

(54) FISHER'S EXACT TEST CALCULATION APPARATUS, METHOD, AND PROGRAM

(71) Applicants: NIPPON TELEGRAPH AND TELEPHONE CORPORATION, Chiyoda-ku (JP); TOHOKU UNIVERSITY, Sendai (JP)

(72) Inventors: Koji Chida, Musashino (JP); Satoshi Hasegawa, Musashino (JP); Koki Hamada, Musashino (JP); Masao Nagasaki, Sendai (JP); Kazuharu Misawa, Sendai (JP)

(73) Assignees: NIPPON TELEGRAPH AND TELEPHONE CORPORATION, Chiyoda-ku (JP); TOHOKU UNIVERSITY, Sendai (JP)

( * ) Notice: Subject to any disclaimer, the term of this patent is extended or adjusted under 35 U.S.C. 154(b) by 1015 days.

(21) Appl. No.: 16/311,395

(22) PCT Filed: Jun. 30, 2017

(86) PCT No.: PCT/JP2017/024119
§ 371 (c)(1),
(2) Date: Dec. 19, 2018

(87) PCT Pub. No.: WO2018/008541
PCT Pub. Date: Jan. 11, 2018

(65) Prior Publication Data
US 2019/0340215 A1    Nov. 7, 2019

(30) Foreign Application Priority Data
Jul. 6, 2016 (JP) .............................. JP2016-134085

(51) Int. Cl.
G06F 16/901    (2019.01)
G06F 21/62    (2013.01)
(Continued)

(52) U.S. Cl.
CPC .......... *G06F 17/18* (2013.01); *G06F 16/9027* (2019.01); *G16B 40/00* (2019.02)

(58) Field of Classification Search
CPC ... G16B 40/20; G06F 16/285; G06F 16/2219; G06F 16/24578; G06F 21/6245;
(Continued)

(56) References Cited

U.S. PATENT DOCUMENTS

2009/0112850 A1    4/2009  Toyoda et al.
2013/0023430 A1*   1/2013  Lenz ................... C12Q 1/6886
                                                          506/9
(Continued)

FOREIGN PATENT DOCUMENTS

WO    WO 2007/126088 A1    11/2007

OTHER PUBLICATIONS

Damgard, Ivan, et al., "Unconditionally secure constant-rounds multi-party computation for equality, comparison, bits and exponentiation", In Proc. 3rd Theory of Cryptography Conference, T C C 2006, vol. 3876 of Lecture Notes in Computer Science, pp. 285-304, Berlin, 2006, Springer-Verlag (Year: 2018).*
(Continued)

*Primary Examiner* — Jeffrey P Aiello
(74) *Attorney, Agent, or Firm* — Oblon, McClelland, Maier & Neustadt, L.L.P.

(57) ABSTRACT

A Fisher's exact test calculation apparatus includes: a condition storage 1 that has stored therein a condition for determining whether a result of Fisher's exact test corresponding to input is significant or not, the input being frequencies in a summary table; and a calculation unit 2 that obtains the result of Fisher's exact test corresponding to the frequencies in the summary table by inputting the frequencies in the summary table to the condition read from the condition storage 1.

4 Claims, 3 Drawing Sheets

(51) Int. Cl.
   *H04L 9/00* (2022.01)
   *G06F 17/18* (2006.01)
   *G16B 40/00* (2019.01)
(58) Field of Classification Search
   CPC .......... G06N 20/00; G06N 20/10; G06N 3/08;
            G06N 7/005; G06N 3/0472; G06N 3/04;
            G06K 9/6267
   USPC ............ 700/1; 702/19, 179; 703/11; 706/12,
            706/52; 707/737, 748, 756
   See application file for complete search history.

(56) References Cited

U.S. PATENT DOCUMENTS

| 2015/0072023 A1* | 3/2015 | Greenberg | A61K 9/0073 424/718 |
|---|---|---|---|
| 2017/0193527 A1* | 7/2017 | Backer | G06F 8/71 |

OTHER PUBLICATIONS

Quinlan, John R., "Induction of decision trees", Machine learning, 1986, p. 81-106. (Year: 1986).*
Extended European Search Report dated Jan. 9, 2020, in Patent Application No. 17824146.9, 6 pages.
Bogdanov, D. et al., "Rmind: a tool for cryptographically secure statistical analysis", International Association for Cryptologic Research (IACR), XP061016368, vol. 20140630:165415, Jun. 30, 2014, 35 pages.
Hamada, K. et al., "Privacy-Preserving Fisher's Exact Test for Genome-Wide Association Study", International Workshop on Genome Privacy and Security, XP009516359, Oct. 15, 2017, 20 pages.
Kamm, L. et al., "A new way to protect privacy in large-scale genome-wide association studies", Bioinformatics, XP055654646, vol. 29, No. 7, Feb. 14, 2013, pp. 886-893.
Park Peter: "Lecture 6: Contingency Tables", Lecture notes for Biomedical Informatics 713/Genetics 212, Fall 2010, XP055851347, Dec. 16, 2015, pp. 1-4, Retrieved from the Internet: URL:https://web.archive.org/web/20151216061115if_/http://compbio.med.harvard.edu:80/BM1713/BM1713%20Lecture%206%20-%20Contingency%20Tables.pdf [retrieved on Oct. 14, 2021].
Craig Gentry, "Fully Homomorphic Encryption Using Ideal Lattices", Stanford University and IBM Watson, XP58164708, 2009, pp. 169-178.
International Search Report dated Sep. 12, 2017 in PCT/JP2017/024119 filed on Jun. 30, 2017.
Karczewski, K., "How to do a GWAS", Lecture note in GENE 210: Genomics and Personalized Medicine, 2015. (5 pages).
Zhang, Y. et al., "Secure Distributed Genome Analysis for GWAS and Sequence Comparison Computation", BMC Medical Informatics and Decision Making, vol. 15, Suppl. 5, p. S4, 2015, pp. 1-12.
Breiman, L. et al., "Classification and Regression Trees (Wadsworth Statistics/Probability)", Wadsworth & Brooks/Cole Advanced Books & Software, (7 pages).
Quinlan, J. R., "Induction of Decision Trees", Machine Learning, vol. 1, 1986, pp. 81-106.
Hastie T. et al., "The Elements of Statistical Learning, Data Mining, Inference, and Prediction" Second Edition, Springer Series in Statistics, 2009, 40 pages.
Damgard, I. et al., "Unconditionally Secure Constant-Rounds Multi-Party Computation for Equality, Comparison, Bits and Exponentiation", In Proc. 3rd Theory of Cryptography Conference, TCC 2006, vol. 3876 of Lecture Notes in Computer Science, Berlin, 2006, Springer-Verlag, ( 20 pages).
Nishide, T. et al., "Multiparty Computation for Interval, Equality, and Comparison Without Bit-Decomposition Protocol", Public Key Cryptography—PKC 2007, 10th International Conference on Practice and Theory in Public-Key Cryptography, 2007, pp. 343-360.
European Office Action dated Nov. 18, 2020 in European Patent Application No. 17 824 146.9, 12 pages.
Koki Hamada, et al., "Privacy Preserving Fisher's Exact Test (2)—for Large Samples" Research Report of Information Processing Society of Japan, Information Processing Society of Japan, XP009513204, vol. 2016—CSEC-74, No. 38, Jul. 7, 2016, 6 pages.
Ali Shahbazi, et al., "Private Computation with Genomic Data for Genome-Wide Association and Linkage Studies" GenoPri Workshop 2016, XP055748519, Nov. 12, 2016, 17 pages.
Felipe Llinares Lopez, et al., "Fast and Memory-Efficient Significant Pattern Mining via Permutation Testing" arxiv.org, Cornell University Library, XP080677993, Feb. 15, 2015, 12 pages.
David J. Wu, et al., "Privately Evaluating Decision Trees and Random Forests" IACR, International Association for Cryptologic Research, vol. 20160526:210652, XP061020820, May 26, 2016, 35 pages.
Japanese Office Action dated Nov. 12, 2019, in Patent Application No. 2018-526334, 4 pages (with English translation).

* cited by examiner

FISHER'S EXACT TEST CALCULATION APPARATUS, METHOD, AND PROGRAM

TECHNICAL FIELD

The present invention relates to techniques for efficiently calculating Fisher's exact test.

BACKGROUND ART

Fisher's exact test is widely known as one of statistical test methods. An application of Fisher's exact test is genome-wide association study (GWAS) (see Non-patent Literature 1, for instance). Brief description of Fisher's exact test is given below.

TABLE 1

|       | X     | Y     | Total         |
|-------|-------|-------|---------------|
| A     | a     | b     | a + b         |
| G     | c     | d     | c + d         |
| Total | a + c | b + d | a + b + c + d (=n) |

This table is an example of a 2×2 summary table that classifies n subjects according to character (X or Y) and a particular allele (A or G) and counts the results, where a, b, c, and d represent frequencies (non-negative integers). In Fisher's exact test, when the following is assumed for a non-negative integer i, $$p_i = \frac{(a+b)!(c+d)!(a+c)!(b+d)!}{n!i!(a+b-i)!(a+c-i)!(d-a+i)!}$$

it is determined whether there is a statistically significant association between the character and a particular allele based on the magnitude relationship between:

$$p = p_a + \sum_{\substack{max(0,a-d) \le i \le min(a+b,a+c) \\ p_i < p_a}} p_i$$

and a threshold T of a predetermined value. In genome-wide association study, a summary table like the above one can be created for each single nucleotide polymorphism (SNP) and Fisher's exact test can be performed on each one of the summary tables. Genome-wide association study involves an enormous number of SNPs on the order of several millions to tens of millions. Thus, in genome-wide association study, there can be a situation where a large quantity of Fisher's exact test is performed.

Meanwhile, in view of the sensitivity or confidentiality of genome information, some prior studies are intended to perform genome-wide association study while concealing genome information via encryption techniques (see Non-patent Literature 2, for instance). Non-patent Literature 2 proposes a method of performing a chi-square test while concealing genome information.

PRIOR ART LITERATURE

Non-Patent Literature

Non-patent Literature 1: Konrad Karczewski, "How to do a GWAS", GENE 210: Genomics and Personalized Medicine, 2015.

Non-patent Literature 2: Yihua Zhang, Marina Blanton, and Ghada Almashaqbeh, "Secure distributed genome analysis for GWAS and sequence comparison computation", BMC Med. Inform. Decis. Mak., 2015.

SUMMARY OF THE INVENTION

Problems to be Solved by the Invention

Since Fisher's exact test requires calculation of min(a+b, a+c)-max(0, a-d)+1 types of $p_i$ and Fisher's exact test can be conducted on individual ones of a large quantity of summary tables particularly in the case of genome-wide association study, it could involve an enormous processing time depending on the computer environment and/or the frequencies in the summary tables.

An object of the present invention is to provide a Fisher's exact test calculation apparatus, method, and program for performing calculations for Fisher's exact test in a more efficient manner than conventional arts.

Means to Solve the Problems

A Fisher's exact test calculation apparatus according to an aspect of the present invention includes: a condition storage that has stored therein a condition for determining whether a result of Fisher's exact test corresponding to input is significant or not, the input being frequencies in a summary table; and a calculation unit that obtains the result of Fisher's exact test corresponding to the frequencies in the summary table by inputting the frequencies in the summary table to the condition read from the condition storage.

Effects of the Invention

By performing precomputation, calculations for Fisher's exact test in main calculation can be performed in a more efficient manner than conventional arts.

DETAILED DESCRIPTION OF THE EMBODIMENT

An embodiment of the present invention is described below with reference to the drawings.

Figure 1:
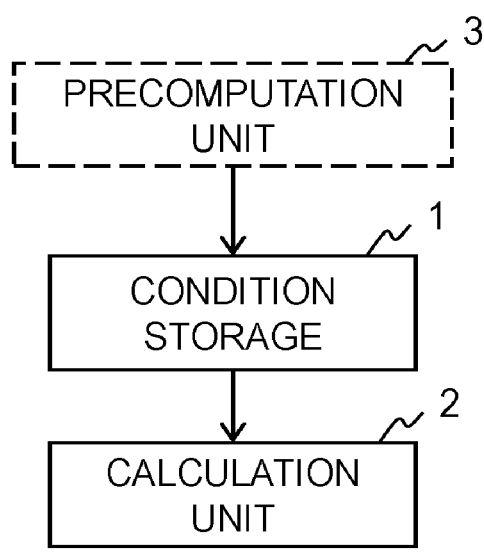
FIG. 1 is a block diagram for describing an example of a Fisher's exact test calculation apparatus.
Figure 2:
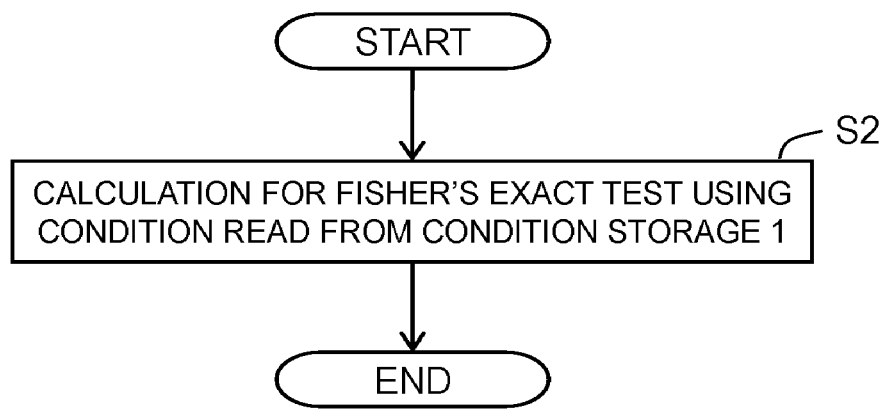
FIG. 2 is a flow diagram for describing an example of a Fisher's exact test calculation method.

As shown in FIG. 1, a Fisher's exact test calculation apparatus includes, for example, a condition storage 1 and a calculation unit 2. A Fisher's exact test calculation method is implemented by the calculation unit 2 of the Fisher's exact test calculation apparatus performing the processing at step S2 described in FIG. 2 and below.

It is assumed that a total sum n of the frequencies in a summary table and the value of a threshold T representing a significance level are predetermined.

<Condition Storage 1>

The condition storage 1 has stored therein a condition for determining whether the result of Fisher's exact test corresponding to input is significant or not, the input being the frequencies in a summary table.

For instance, the result of Fisher's exact test is determined in advance for each set (a', b', c', d') of all the non-negative integers that satisfy n=a'+b'+c'+d', and (a', b', c', d') and the corresponding result of Fisher's exact test are stored in the condition storage 1 in association with each other. The Fisher's exact test calculation apparatus may include a precomputation unit 3 for performing this precomputation.

Figure 3:
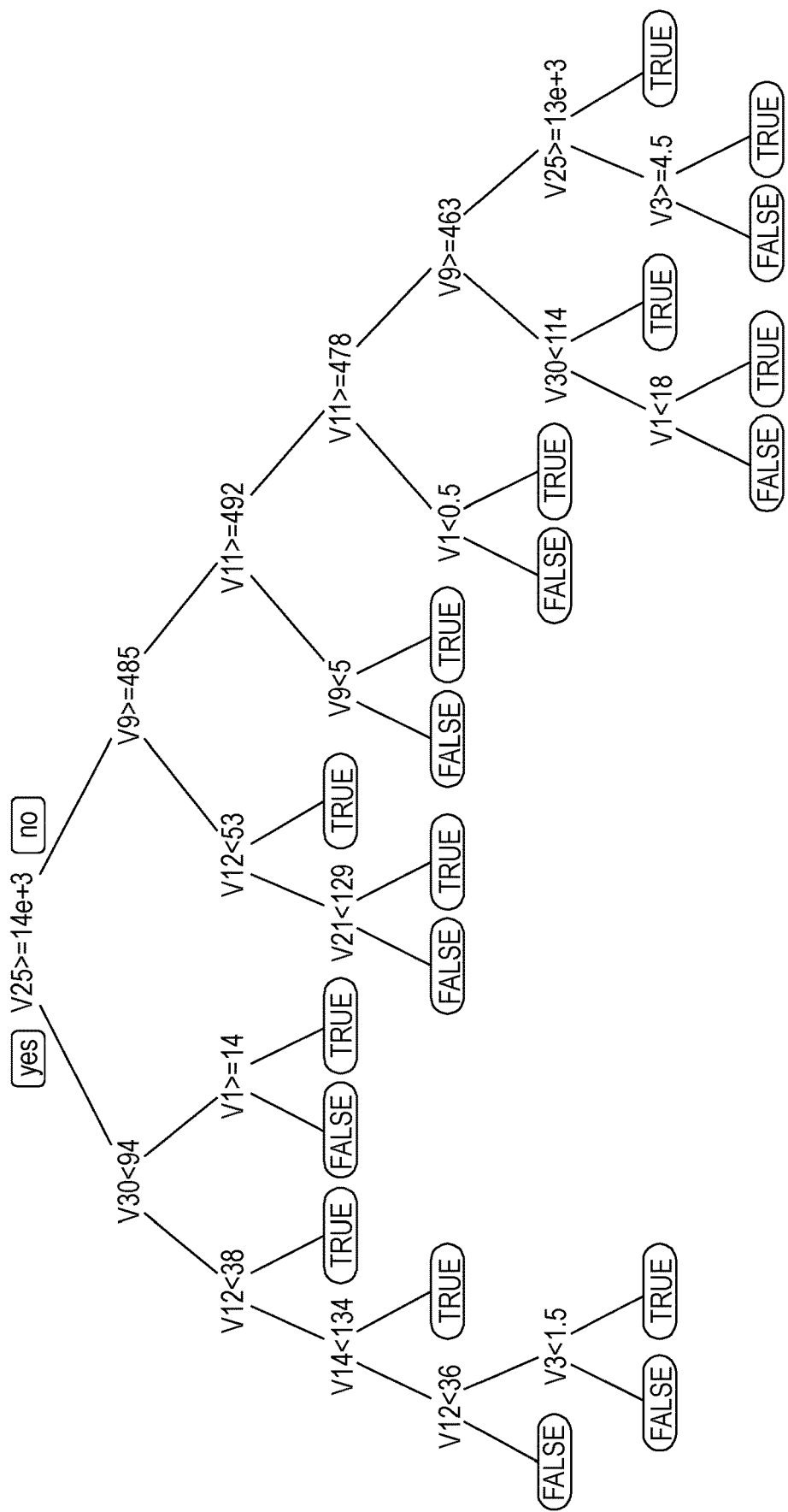
FIG. 3 is a diagram showing an example of a decision tree.

The condition stored in the condition storage 1 may be a decision tree with conditional expressions assigned to a root node and internal nodes and a result of Fisher's exact test assigned to each leaf node. An example of a decision tree for a case with n=50 and the predetermined threshold T=$10^{-8}$ is shown in FIG. 3. Such a decision tree may be created using an existing machine learning method.

For instance, such a tree can be created with the methods described in Reference Literatures 1 to 3 based on the sets (a', b', c', d') of all the non-negative integers satisfying n=a'+b'+c'+d' and on a formula for determining the result of Fisher's exact test.

Reference Literature 1: Leo Breiman, Jerome H. Friedman, Richard A. Olshen, Charles J. Stone, "Classification and Regression Trees (Wadsworth Statistics/Probability)", Wadsworth & Brooks/Cole Advanced Books & Software.

Reference Literature 2: John R. Quinlan, "Induction of decision trees", Machine learning, 1986, P. 81-106.

Reference Literature 3: Trevor Hastie, Robert Tibshirani, Jerome Friedman, "The Elements of Statistical Learning Data Mining, Inference, and Prediction, Second Edition", Springer Series in Statistics.

In FIG. 3, the conditional expressions assigned to the root node and the internal nodes are formulas each representing the magnitude relationship between one of V1=a, V3=c, V9=ad, V11=bc, V12=bd, V14=cd, V21=abc, V25=$ad^2$, V30=bcd and the threshold corresponding to each node. In FIG. 3, 14e+3 means 14*$10^3$ and 13e+3 means 13*$10^3$. For the decision tree of FIG. 3, it is assumed that, when the frequencies (a, b, c, d) in a summary table to be subjected to Fisher's exact test are input to the conditional expression corresponding to a certain node, transition is made to the child node on the left side of that node if the conditional expression holds, and to the child node on the right side of that node if the conditional expression does not hold. In the decision tree of FIG. 3, "FALSE" at a leaf node means p>T and the result of Fisher's exact test is not significant, and "TRUE" at a leaf node means p≤T and the result of Fisher's exact test is significant.

<Calculation Unit 2>

The calculation unit 2 obtains the result of Fisher's exact test corresponding to the frequencies in the summary table subjected to Fisher's exact test by inputting the frequencies in the summary table to the condition read from the condition storage 1 (step S2).

For example, when (a', b', c', d') and the corresponding result of Fisher's exact test are stored in the condition storage 1 in association with each other, the calculation unit 2 obtains the result of Fisher's exact test corresponding to the frequencies (a, b, c, d) in the input summary table by referencing the condition storage 1. More specifically, the calculation unit 2 obtains the result of Fisher's exact test corresponding to the same frequencies (a', b', c', d') as the frequencies (a, b, c, d) in the input summary table by referencing the condition storage 1, and outputs it as the result of Fisher's exact test corresponding to the frequencies (a, b, c, d) in the input summary table. Alternatively, only the frequencies in summary tables for which the result of Fisher's exact test is significant may be stored in the condition storage 1, and the result of Fisher's exact test may be determined to be significant if the same frequencies (a', b', c', d') as the frequencies (a, b, c, d) in the input summary table are present in the condition storage 1. Similarly, the frequencies in summary tables for which the result of Fisher's exact test is not significant may be stored.

In a case where the condition storage 1 stores a decision tree with conditional expressions assigned to the root node and the internal nodes and a result of Fisher's exact test assigned to each leaf node, the calculation unit 2 may output the result of Fisher's exact test assigned to the leaf node which is determined by a value obtained by inputting the frequencies in the summary table to the conditional expressions assigned to the root node and the internal nodes.

For example, processing may be performed as described below when data for the decision tree of FIG. 3 is stored in the condition storage 1 as the condition and this decision tree of FIG. 3 is used to obtain the result of Fisher's exact test corresponding to the frequencies (a, b, c, d) in the input summary table.

The calculation unit 2 first determines by calculation whether the conditional expression "V25>=14e+3" at the topmost or root node, that is, $ad^2$≥14000, is satisfied or not. If it is satisfied, the calculation unit 2 proceeds to the conditional expression of the child node on the left side of the root node, and if it is not satisfied, the calculation unit 2 proceeds to the conditional expression of the child node on the right side of the root node. Subsequently, the calculation unit 2 repeatedly performs a similar process until it reaches a leaf node. The calculation unit 2 then outputs the result of Fisher's exact test corresponding to the leaf node reached.

In the example of a decision tree in FIG. 3, it can be seen that the result of Fisher's exact test is obtained with no more than seven magnitude comparisons. In contrast, calculation of $$p = p_a + \sum_{\substack{max(0,a-d) \leq i \leq min(a+b,a+c) \\ p_i < p_a}} p_i$$

requires determination of about n/2=25 $p_i$'s in the worst case. $p_i$ in turn consists of multiplications and divisions of nine factorial values, which can be efficiently determined by taking a logarithm and performing precomputation as shown below.

$$p_i = \frac{(a+b)!(c+d)!(a+c)!(b+d)!}{n!i!(a+b-i)!(a+c-i)!(d-a+i)!} \quad \text{Formula A}$$

hence, $$\log p_a = \sum_{j=1}^{a+b} \log j + \sum_{j=1}^{c+d} \log j + \sum_{j=1}^{a+c} \log j + \sum_{j=1}^{b+d} \log j -$$

$$\sum_{j=1}^{n} \log j - \sum_{j=1}^{a} \log j - \sum_{j=1}^{b} \log j - \sum_{j=1}^{c} \log j - \sum_{j=1}^{d} \log j$$

thus, by precomputing $\Sigma_{i=1}^{k} \log j$ for k=0-, 1, 2, ..., n and determining log $p_a$ with the precomputed value, it can be calculated just by additions and subtractions of precomputed values. Then, $p_i$ is determined from log $p_i$. Here, $\Sigma_{i=1}^{0}$ log j=0 holds.

For determining $p_i$, the aforementioned computation requires nine matching processes, eight additions and subtractions, and determination of $p_i$ from log $p_i$. Accordingly, at least 25×9=225 matching processes are required, meaning a number of calculations 225/7=32.1 times as large as just seven magnitude comparisons. Further considering that a matching process takes a processing time equivalent to or longer than that of magnitude comparison, use of a decision tree is expected to lead to a shorter processing time as well.

The calculation unit 2 may also perform calculations for obtaining the result of Fisher's exact test corresponding to the frequencies (a, b, c, d) in the input summary table subjected to Fisher's exact test while keeping the frequencies (a, b, c, d) concealed via secure computation.

Such a calculation can be carried out by combining encryption techniques capable of magnitude comparison while concealing the input and output. In the following, magnitude comparison with the input and output concealed (hereinafter abbreviated as input/output-concealed magnitude comparison) is described. Assume that two values x and y for magnitude comparison are the input and at least one of x and y is encrypted such that its real numerical value is not known. In the present description, only x is encrypted, which is denoted as E(x). The result of magnitude comparison, which is to be output, is defined as:

$$z = \begin{cases} 1 & \text{if } x \geq y \\ 0 & \text{otherwise} \end{cases}$$

That is to say, the input/output-concealed magnitude comparison means determining cipher text E(z) for the result of magnitude comparison by using E(x),y as the input and without decrypting E(x). When z is the result to be finally obtained, E(z) is appropriately decrypted. An example of such input/output-concealed magnitude comparison is the method described in Reference Literatures 4 and 5, for example.

Reference Literature 4: Ivan Damgard, Matthias Fitzi, Eike Kiltz, Jesper B. Nielsen, Tomas Toft, "Unconditionally secure constant-rounds multi-party computation for equality, comparison, bits and exponentiation", In Proc. 3rd Theory of Cryptography Conference, T C C 2006, volume 3876 of Lecture Notes in Computer Science, pages 285-304, Berlin, 2006, Springer-Verlag Reference Literature 5: Takashi Nishide, Kazuo Ohta, "Multiparty Computation for Interval, Equality, and Comparison Without Bit-Decomposition Protocol", Public Key Cryptography—PKC 2007, 10th International Conference on Practice and Theory in Public-Key Cryptography, 2007, P. 343-360

A method for determining the result of Fisher's exact test from the decision tree of FIG. 3 using input/output-concealed magnitude comparison is described below.

Assume that the input is cipher text (E(a), E(b), E(c), E(d)) of the frequencies (a, b, c, d) in a summary table and data on the decision tree of FIG. 3. When input/output-concealed magnitude comparison is not used, it is first determined by calculation whether the conditional expression "V25>=14e+3" at the topmost or root node, that is, $ad^2 \geq 14000$, is satisfied or not as described above. If it is satisfied, the flow proceeds to the conditional expression of the child node on the left side of the root node, and if it is not satisfied, the flow proceeds to the conditional expression of the child node on the right side of the root node. Subsequently, a similar process is repeatedly performed until a leaf node is reached. Then, the result of Fisher's exact test corresponding to the leaf node reached is output.

When this is carried out using input/output-concealed magnitude comparison, $E(ad^2)$ is first calculated for the conditional expression $ad^2 \geq 14000$ from the input E(a), E(d) without decrypting them. As this method is described in Reference Literatures 4 and 5, for instance, specific description is omitted. Then, using input/output-concealed magnitude comparison, $E([ad^2 \geq 14000])$ is calculated from $E(ad^2)$ and from 14000 of the conditional expression.

Here, $[ad^2 \geq 14000]$ is 1 if $ad^2 \geq 14000$, and 0 otherwise. The flow next proceeds to either the lower left conditional expression "V30<94" or the lower right conditional expression "V9>=485"; however, to which of them to proceed is not known because the value of $[ad \geq 14000]$ is concealed. Thus, for each one of all the paths that start at the root node and reach a leaf node assigned with TRUE, calculations are performed to determine whether the conditional expressions of the nodes on that path are satisfied, and then whether a leaf node assigned with TRUE has been reached is output as the final output, namely the Fisher's exact test result.

For example, in the case of the path that reaches the leftmost leaf node assigned with TRUE, the first four of the conditional expressions, "V25≥14e+3", "V30<94", "V12<38", "V14<134", "V12<36", and "V3<1.5" should be Yes and the remaining two should be No. Thus, conditions are established so that cipher text of "1" will be returned if the first four are Yes and the remaining two are No, and cipher text of "0" will be returned otherwise. For example, for the sake of simplicity, the conditional expressions "V12<36" and "V3<1.5" are replaced with "V12≥36" and "V3≥1.5" respectively so that cipher text of "1" will be returned if all the conditional expressions result in Yes. Data on the decision tree after such replacement is stored in the condition storage 1 as the condition in advance.

Here, for the conditional expressions "V25≥14e+3", "V30<94", "V12<38", "V14<134", "V12≥36", and "V3≥1.5", cipher text of their results (referred to as $E(z_1)$, $E(z_2)$, $E(z_3)$, $E(z_4)$, $E(z_5)$, and $E(z_6)$, respectively) is determined using input/output-concealed magnitude comparison. In order to return cipher text of "1" only if all the conditional expressions result in Yes, $E(z_1 z_2 z_3 z_4 z_5 z_6)$ is determined from $E(z_1)$, $E(z_2)$, $E(z_3)$, $E(z_4)$, $E(z_5)$, and $E(z_6)$. That is, the calculation unit 2 performs multiplication while keeping the content of the cipher text concealed. As this method is also described in Reference Literatures 4 and 5, for instance, specific description is omitted. Subsequently, a similar process is performed for all the paths that reach a leaf node assigned with TRUE, and multiplication is further performed while concealing the content of the cipher text for all of the resulting cipher text (16 patterns of cipher text that reach TRUE, including $E(z_1 z_2 z_3 z_4 z_5 z_6)$).

The result is cipher text of "1" if the Fisher's exact test result is TRUE and cipher text of "0" otherwise, so that the Fisher's exact test result can be obtained by decrypting the result. That is, if such calculation is performed using cipher text (E(a), E(b), E(c), E(d)) of the frequencies (a, b, c, d) in an input summary table and there is a path for which the result of decrypting $E(z_1 z_2 z_3 z_4 z_5 z_6)$ is 1, it may be determined that the result of Fisher's exact test for that input summary table is significant.

Further, in order to also conceal which leaf node has been reached, a logical sum for plaintext, $\cup z_{1j} z_{2j} z_{3j} z_{4j} z_{5j} z_{6j}$, for example, is determined by secure computation for the cipher text $E(z_{1j} z_{2j} z_{3j} z_{4j} z_{5j} z_{6j})$ (j=1, 2, . . . ) obtained for all the paths that reach a leaf node assigned with TRUE. That is, this makes use of the fact that $\cup z_{1j} z_{2j} z_{3j} z_{4j} z_{5j} z_{6j} = 1$ if the result of decryption is 1 even for only one cipher text $E(z_{1j} z_{2j} z_{3j} z_{4j} z_{5j} z_{6j})$ (j=1, 2, . . . ). Secure computation for logical sum may be performed by the method described in Reference Literature 1, for example.

That is, the result may also be obtained in the following manner. Results indicative of being significant or not in Fisher's exact test are assigned to leaf nodes. Conditional expressions are assigned to the respective nodes on a path from the root node to a leaf node. Starting from the root node, by inputting the frequencies in a summary table to the conditional expression of each node and branching from the node, a path to one leaf node can be followed. This can obtain the result assigned to the leaf node, indicative of being significant or not in Fisher's exact test. The calculation unit 2 can evaluate the conditional expression of each node and obtain a path leading to one leaf node while concealing the frequencies in the summary table, thus obtaining the result of Fisher's exact test while concealing the frequencies in the summary table.

In this manner, by determining the correspondence between the frequency patterns of summary tables and the results of Fisher's exact test (for example, a binary value of TRUE or FALSE) in advance and creating a condition under which the result of Fisher's exact test is TRUE (or FALSE), main calculation (calculation excluding preliminary calculation portions) can obtain the result of Fisher's exact test just by inputting the frequencies in a summary table to the condition and performing calculations, without calculating $p_i$. As calculation of $p_i$ is not necessary, calculations for Fisher's exact test can be performed efficiently.

In addition, by making precomputation results available for public use, computers with lower computational ability on which execution of Fisher's exact test has been difficult may become able to perform Fisher's exact test by referencing the precomputation results. Specifically, effects such as reduced usage of calculation resources and/or a shortened processing time are expected to be achieved.

Further, the above-described concealment enables Fisher's exact test to be executed while concealing genome information and various kinds of associated data, for example. This allows, for example, multiple research institutions to obtain the result of executing Fisher's exact test on combined data while concealing the genome data possessed by the individual institutions and without revealing it to one another, which potentially leads to provision of execution environments for genome analysis of an extremely high security level and hence further development of medicine.

[Program and Recording Medium]

The processes described in connection with the Fisher's exact test calculation apparatus and method may be executed not only in a chronological order in accordance with the order of their description but in a parallel manner or separately depending on the processing ability of the apparatus executing the processes or any necessity.

Also, when the processes of the Fisher's exact test calculation apparatus are to be implemented by a computer, the processing specifics of the functions to be provided by the Fisher's exact test calculation apparatus are described by a program. By the program then being executed by the computer, the processes are embodied on the computer.

The program describing the processing specifics may be recorded on a computer-readable recording medium. The computer-readable recording medium may be any kind of media, such as a magnetic recording device, an optical disk, a magneto-optical recording medium, and semiconductor memory.

Processing means may be configured through execution of a predetermined program on a computer or at least some of the processing specifics thereof may be embodied in hardware.

It will be appreciated that modifications may be made as appropriate without departing from the scope of the present invention.

INDUSTRIAL APPLICABILITY

The Fisher's exact test calculation apparatus and method of the present invention are applicable to performing Fisher's exact test via secure computation while keeping information on summary tables concealed in an analysis utilizing Fisher's exact test, for example, genome-wide association study, genome analysis, clinical research, social survey, academic study, analysis of experimental results, marketing research, statistical calculations, medical information analysis, customer information analysis, and sales analysis. In the case of genome-wide association study, the input to the Fisher's exact test calculation apparatus and method may be the frequencies in a 2×2 summary table that classifies n subjects according to whether they have a particular character and whether they have a particular allele (for example, A or G) and counts the results, for example.

What is claimed is:

1. A Fisher's exact test calculation system comprising:
a memory that includes a condition storage that has stored therein a condition for determining whether a result of Fisher's exact test corresponding to input is significant or not, the input being frequencies in a summary table; and
processing circuitry that obtains the result of Fisher's exact test corresponding to the frequencies in the summary table by inputting the frequencies in the summary table to the condition read from the condition storage,
wherein
the condition is a decision tree with conditional expressions assigned to a root node and internal nodes and a result of Fisher's exact test assigned to each leaf node, and
the processing circuitry outputs the result of Fisher's exact test assigned to a leaf node which is determined by a value obtained by inputting the frequencies in the summary table to the conditional expressions assigned to the root node and the internal nodes while keeping the frequencies in the summary table concealed via secure computation.

2. The Fisher's exact test calculation apparatus according to claim 1, wherein
conditional expressions are assigned to the root node and the internal nodes such that, for a leaf node assigned with a result of Fisher's exact test indicative of being significant, a predetermined value will be obtained by inputting the frequencies in the summary table to the conditional expressions assigned to the root node and the internal nodes on a path from that leaf node to the root node, and
the processing circuitry determines whether there is a leaf node for which the predetermined value is obtained by inputting the frequencies in the summary table to the conditional expressions assigned to the root node and the internal nodes on the path from the leaf node to the root node while concealing the frequencies in the summary table, and if there is such a leaf node, obtains a result that the result of Fisher's exact test for the summary table is significant.

3. A non-transitory computer-readable medium that stores a program for causing a computer to function as the units of Fisher's exact test calculation system according to claim 1.

4. A Fisher's exact test calculation method implemented by a system having a memory that includes a condition storage that has stored therein a condition for determining whether a result of Fisher's exact test corresponding to input is significant or not, the input being frequencies in a summary table, the method comprising:

obtaining, by processing circuitry, the result of Fisher's exact test corresponding to the frequencies in the summary table by inputting the frequencies in the summary table to the condition read from the condition storage, wherein the condition is a decision tree with conditional expressions assigned to a root node and internal nodes and a result of Fisher's exact test assigned to each leaf node, and the method further includes outputting the result of Fisher's exact test assigned to a leaf node which is determined by a value obtained by inputting the frequencies in the summary table to the conditional expressions assigned to the root node and the internal nodes while keeping the frequencies in the summary table concealed via secure computation.

\* \* \* \* \*